United States Patent
Sander et al.

[11] Patent Number: 6,140,539
[45] Date of Patent: Oct. 31, 2000

[54] PREPARATION OF AMINES

[75] Inventors: Michael Sander, Ruhland; Dietmar Peisker, Senftenberg; Klaus Werner, Schwarzheide; Holger Braunsberg, Senftenberg; Gunter Georgi, Lauchhammer; Ulrich Penzel, Tettau, all of Germany

[73] Assignee: BASF Aktiengesellschaft, Ludwigshafen, Germany

[21] Appl. No.: 09/518,620

[22] Filed: Mar. 3, 2000

[30] Foreign Application Priority Data

Mar. 3, 1999 [DE] Germany .................. 199 09 168

[51] Int. Cl.[7] .................. C07C 209/00
[52] U.S. Cl. .................. 564/421; 564/417; 564/422; 564/494; 564/495
[58] Field of Search .................. 564/417, 421, 564/422, 494, 495

[56] References Cited

U.S. PATENT DOCUMENTS

| | | |
|---|---|---|
| 2,564,331 | 8/1951 | Hawley et al. . |
| 3,235,515 | 2/1966 | Taylor et al. . |
| 4,792,626 | 12/1988 | Becher et al. . |
| 4,956,328 | 9/1990 | Frohning et al. . |
| 5,736,484 | 4/1998 | Polanek et al. . |

FOREIGN PATENT DOCUMENTS

| | | |
|---|---|---|
| 1 211 757 | 9/1986 | Canada . |
| 0 098 681 A2 | 1/1984 | European Pat. Off. . |
| 0 124 010A1 | 11/1984 | European Pat. Off. . |
| 0 335 222 B1 | 10/1989 | European Pat. Off. . |
| 0 672 452B1 | 9/1995 | European Pat. Off. . |
| 126 891 | 9/1975 | German Dem. Rep. . |
| 0 152 065 | 7/1980 | German Dem. Rep. . |
| 1257753 | 4/1963 | Germany . |
| 2 135 154 | 2/1973 | Germany . |
| 35 37 247A1 | 4/1987 | Germany . |
| 283185 | 7/1969 | U.S.S.R. . |

*Primary Examiner*—Samuel Barts
*Attorney, Agent, or Firm*—Fernando A. Borrego

[57] ABSTRACT

In a process for preparing amines, in which at least one compound containing at least one nitro group is reacted with hydrogen in the presence of a supported catalyst comprising, as catalytically active metal, nickel, if desired together with at least one metal of transition group I, V, VI and/or VIII, the reduced and stabilized supported catalyst comprises nickel crystallites having a bimodal nickel crystallite size distribution having maxima at 30–80 Angström and 81–150 Angström on a support comprising $ZrO_2$, $ZrO_2$—$HfO_2$ and/or $SiO_2$—$ZrO_2$ and/or $SiO_2$—$ZrO_2$—$HfO_2$ and in the reduced and passivated state has a nickel content of 60–80 percent by mass, an $SiO_2$ content of 0–20 percent by mass, a $ZrO_2$ content of 0–40 percent by mass, an $HfO_2$ content of 0–4 percent by mass and after further reduction for one hour at 100° C. has a degree of reduction of at least 70%.

12 Claims, No Drawings

PREPARATION OF AMINES

FIELD OF THE INVENTION

The invention relates to a process for preparing amines by hydrogenation of the corresponding nitro compounds.

BACKGROUND TO THE INVENTION

The preparation of amines, particularly of aromatic monoamines, diamines and/or polyamines, by catalytic hydrogenation of the corresponding mononitro, dinitro and/or polynitro compounds has been known for a long time and is widely described in the literature.

The industrially customary preparation of monoamines, diamines and/or polyamines by reaction of the corresponding nitro compounds with hydrogen liberates a considerable amount of heat. The hydrogenation is therefore usually carried out industrially at the lowest possible temperatures using hydrogenation catalysts in the liquid phase. Here, the compound to be reduced is mixed with the catalyst in a solvent and reduced batchwise in an autoclave or continuously in a loop reactor, a bubble column or a reactor cascade. These catalytic hydrogenation processes are usually carried out at temperatures of from 353 to 500K and pressures of from $5 \cdot 10^5$ to $5 \cdot 10^6$ Pa with addition of solvents such as water, alcohols, hydrocarbons or previously hydrogenated products. These previously known processes suffer from a series of disadvantages, for example the necessity of discharging and particularly of discarding deactivated catalyst, which leads to catalyst losses. Furthermore, the secondary reactions which frequently occur and lead to the formation of interfering substances, e.g. tar-like constituents, and thus to reductions in yield are a problem in many of the processes used hitherto. Hydrogenation catalysts used are, as described, for example, in EP-A-0 124 010, preferably metals of transition group VIII of the Periodic Table, in particular Raney iron, Raney cobalt and Raney nickel.

In order to reduce these disadvantages, the installation of the catalyst in a fixed bed is known. Thus, DE-OS 2 135 154 describes the hydrogenation of a nitro compound either alone or in the presence of a diluent in the liquid state in a tube reactor in the presence of a palladium catalyst on spinel in a fixed bed. When this palladium catalyst on spinel is used, the preparation of the catalyst is very complicated and targeted fixing on the support is only sometimes possible. Furthermore, this fixed-bed hydrogenation leads to low hydrogenation yields and to the formation of high-boiling by-products. Examples which may be mentioned in this context are hydrogenolytic cleavages, ring hydrogenations or the formation of high molecular weight, tar-like substances. As a result of the strongly exothermic reaction of the nitro groups and the high reaction rate at relatively high temperatures, explosion-like secondary reactions can also occur.

In order to avoid these undesirable secondary reactions as far as possible, the industrial hydrogenation of nitro compounds has therefore generally been carried out at relatively low temperatures.

The most favorable known process variant for the hydrogenation of nitro compounds is the continuous liquid-phase process having a circuit for the reaction mixture between a reactor with intensive stirring and a decantation vessel for returning the catalyst to the reactor. However, the catalysts used here are relatively quickly broken down under the mechanical stress in the reactor to particle sizes which can no longer be sedimented in the gravity separator and to a large extent have to be taken off together with the hydrogenation product from the upper part of the decantation vessel and transferred to the work-up. In addition, the known processes (BE-A-0 846 341) operate at relatively high catalyst concentrations in the reaction solution. The high catalyst concentrations in the reaction mixture during the hydrogenation are necessary since there is no control parameter for regulating the concentration of nitro groups in the reactor. The reactors are therefore operated under conditions which ensure that all of the nitro compound fed into the reaction system is hydrogenated immediately, so that the concentration of nitro groups in the reaction mixture is about zero.

Various catalyst systems are employed in the processes which have been described; Ni-containing catalysts are most frequently used. The hydrogenation of 2,4- and 2,6-dinitrotoluene in the presence of the catalysts Pd/C, Raney nickel, Raney cobalt and platinum black is disclosed, for example, in JP-A-5 513 333. A supported Ni/kieselguhr catalyst for the hydrogenation of dinitrobenzophenone to give the diamine is described in EP-A-98 681.

DE 3 537 247 A describes the hydrogenation of dinitro compounds in the presence of modified Raney nickel catalysts to give the diamines. The preferred catalyst system comprises not only nickel but also iron, chromium, copper, molybdenum, tungsten, vanadium, titanium, niobium, rhenium, ruthenium, zirconium and/or hafnium.

DD 152 065 teaches the use of an $Ni-SiO_2$ catalyst having a specific particle size distribution for the hydrogenation of nitroaromatics.

EP 0 335 222 teaches the use of supported $Ni-Al_2O_3/ZrO_2$ catalysts for the hydrogenation of nitrites, aromatics, nitro compounds and olefins. This document claims, in particular, the simultaneous precipitation of Ni, Zr and Al on supports, with particular attention being paid to homogeneous precipitation of the components.

$Ni-Al_2O_3-ZrO_2$ catalysts are described in SU-PS 283 185. They are prepared by precipitation of Ni and $Al_2O_3$ on $ZrO_2$.

According to U.S. Pat. No. 2,564,331, an $Ni-ZrO_2$ catalyst is prepared by precipitation of a nickel carbonate and zirconium carbonate mixture with subsequent washing, drying and reduction at from 250 to 350° C. The catalyst contains a maximum of 10% $ZrO_2$.

DE-B 1 257 753 likewise describes the precipitation of insoluble carbonates. The precipitation is triggered by evaporation of $CO_2$ and $NH_3$ from a mixed salt solution of ammonium zirconyl carbonate and nickel ammine carbonate.

EP 0 672 452 discloses catalysts for the hydrogenation of organic compounds, which catalysts contain essentially from 65 to 80% of Ni, calculated as NiO, from 10 to 25% of silicon, calculated as $SiO_2$, from 2 to 10% of zirconium, calculated as $ZrO_2$, and 0–10% of aluminum calculated as $Al_2O_3$, with the sum of the $SiO_2$ content and the $Al_2O_3$ content being at least 15%.

A disadvantage of all previously known Ni-containing catalyst systems is the unsatisfactory mechanical and/or chemical stability of the support material used. Thus, catalyst abrasion, a high fines content, poor sedimentation properties, catalyst discharge, leaching of the support material and/or rapid deactivation of the catalyst represent the typical problems of all previously used processes for the hydrogenation of nitro compounds in a suspension process.

The performance limit of the catalyst used for hydrogenation can be recognized only imprecisely during the reaction. On reaching the performance limit of the catalyst, there is an extraordinarily rapid increase in the concentration of nitro groups. The increasing concentrations of nitro compound in turn have a poisoning effect on the quantities of catalyst present in the reaction system. As a result, the reaction rate drops further and the concentration of nitro compounds accordingly increases even more rapidly when the rate at which nitro compounds are fed in remains constant. The known methods of controlling and regulating the concentration of nitro groups are too sluggish to avoid the rapid rise in the concentration of nitro groups in these cases. Even if a sufficiently low concentration of nitro compounds in the reaction mixture has been measured, this measurement does not indicate whether the performance limit of the catalyst has been reached or exceeded. If high concentrations of nitro groups are present in the reaction mixture, there is the risk that further addition of catalyst to the reaction system could cause rapid heating of the reaction mixture as a result of the high reaction rate. The heat of reaction liberated within a relatively short time in such cases can then no longer be removed by the heat exchanger system installed in the reactor. There is a sharp increase in the pressure in the reactor which can lead to destruction of the plant. Simply monitoring the concentration of nitro groups in the reaction mixture therefore does not give sufficient safety.

These safety problems can be seen to be even more critical if one takes into account the fact that the catalytic activity of the catalysts used can fluctuate greatly as a result of small changes in their preparation or their activation even within a production batch.

In the known processes for the hydrogenation of nitro compounds, attempts are made to make the reaction system safe by means of a considerable excess of catalyst over the amount required by reaction kinetics. In the known processes, it is usual to employ catalyst concentrations in the range from 5 to 15% by weight, based on the reaction mixture. As a result of this high catalyst concentration, the total amount of nitro compound metered in continuously will be hydrogenated completely to a high degree of probability. Accumulation of nitro compounds in the reaction mixture, which can lead to strong heat evolution and thus to a runaway reaction in the reaction vessel, is thus largely avoided. However, a significant disadvantage of this procedure is a high catalyst consumption. The high catalyst concentrations in the reaction mixture additionally result in deposits and solidified catalyst on reactor parts where flow is unfavorable and at constrictions in the reaction system. These deposits lead to blockages in the reactor and can cause a shut down of the entire hydrogenation. Finally, the high catalyst concentrations in the reaction mixture also cause a high discharge of catalyst from the reactor. The catalyst material discharged with the hydrogenated product is highly active, but cannot be returned to the reaction system. On the other hand, it causes considerable difficulties in further processing of the hydrogenation products, for example in the distillation columns. In plants for the hydrogenation of nitro compounds in which the hydrogenation product is circulated between a hydrogenation reactor and a sedimentation vessel for return of the sedimented catalyst, blockages in the return line between reactor and gravity separator occur when using $SiO_2$- and/or $Al_2O_3$- supported catalysts and particularly at relatively high reaction temperatures without addition of alcoholic solvents, hydrocarbons, etc., since the amphoteric catalyst support is leached by the basic reaction medium, thus leading to catalyst agglomeration and conglutination. This results in an additional loss of hydrogenation-active surface and thus a further reduction in the operating life of the catalyst. Likewise, the formation of Ni-containing silicates and/or aluminates can be observed and these deposit primarily in the heat exchangers of the production plant.

A further disadvantage of the known processes employing high catalyst concentrations is the increased formation of by-products which is further promoted by the addition of alcoholic solvents. This greatly reduces the yield of the desired hydrogenation product. In addition, hydrogenation products having a high by-product content incur enormous additional costs for purification of the desired end products. Furthermore, there are additional losses of amine since considerable amounts of the desired amines are still present in the by-products which have been separated off if the effort expended for the purification is not to be too high. The avoidance of additional solvents is therefore desirable.

It is an object of the present invention to develop an improved, industrially usable process for the trouble-free preparation of aromatic and/or aliphatic amines having very good processing properties by catalytic hydrogenation of the amines' parent nitro compounds under customary process conditions in customary reactors using hydrogenation catalysts in the liquid phase, in the presence or absence of a solvent, which process has a low catalyst consumption and largely avoids secondary reactions and enables an optimum catalyst balance to be set and inactive catalyst fractions to be optimally separated.

We have found that this object is achieved by the process of the present invention in which a specific hydrogenation catalyst is used.

The present invention provides a process for preparing amines, in particular aromatic amines, in which at least one compound containing at least one nitro group is hydrogenated in the presence of a supported catalyst comprising, as catalytically active metal, nickel, if desired together with at least one metal of transition group I, V, VI and/or VIII, wherein the reduced and stabilized supported catalyst comprises nickel crystallites having a bimodal nickel crystallite size distribution having maxima at 30–80 Angstrom and 81–150 Angstrom on a support comprising $ZrO_2$, $ZrO_2$—$HfO_2$ and/or $SiO_2$—$ZrO_2$ and/or $SiO_2$—$ZrO_2$—$HfO_2$ and in the reduced and passivated state has a nickel content of 60–80 percent by mass, an $SiO_2$ content of 0–20 percent by mass, a $ZrO_2$ content of 0–40 percent by mass, an $HfO_2$ content of 0–4 percent by mass and after further reduction for one hour at 100° C. has a degree of reduction of at least 70%.

It goes without saying that the content of at least one of the compounds of which the support is composed is not equal to 0 percent by mass.

For the purposes of the present invention, a bimodal particle size distribution is a particle size distribution whose distribution curve has two maxima.

For the purposes of the present invention, the reduced and passivated state of the catalyst means that the catalyst has been activated after its preparation but, since it is usually not stable on storage in this state, the active centers have then been passivated, for example by passing oxygen or carbon dioxide over it.

The catalyst used according to the present invention is preferably used in an amount of from 0.1 to 5% by weight, preferably from 0.2 to 2% by weight, based on the reaction mixture.

The reaction mixture is, for the purposes of the present invention, the total amount of compounds present in the reactor, including starting materials and final product, solvents and water.

The process of the present invention can be carried out continuously or batchwise using customary reactors under customary process conditions such as pressure and temperature, preferably low temperatures.

The hydrogenation of the present invention is preferably carried out at pressures in the range from 10 to about 40 bar, more preferably from 20 to 25 bar.

The hydrogenation of the present invention is preferably carried out at a temperature in the range from 80 to 200° C., particularly preferably in the range from 90 to 160° C. and in particular in the range from 100 to 140° C.

The hydrogenation is usually carried out in the form of a continuous liquid-phase hydrogenation in customary and suitable reactors. Examples of reactors used are stirred vessels or loop reactors, for example loop Venturi reactors.

As hydrogenation gases, it is possible to use any gases which comprise free hydrogen and contain no harmful amounts of catalyst poisons such as CO. Thus, for example, reformer tailgases can be used. However, preference is given to using pure hydrogen as hydrogenation gas.

The amines formed in the hydrogenation are taken continuously or discontinuously from the hydrogenation process and are subjected to a work-up, for example a distillation.

In the process of the present invention, preference is given to using aromatic nitro compounds having one or more nitro groups and from 1 to 18, preferably from 6 to 18, carbon atoms in the molecule, for example nitrobenzenes such as o-, m-, p-nitrobenzene, 1,3-dinitrobenzene, nitrotoluenes such as 2,4-, 2,6-dinitrotoluene, 2,4,6-trinitrotoluene, nitroxylenes such as 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes such as 1-, 2-nitronaphthalene, 1,5 and 1,8-dinitronaphthalene, chloronitrobenzenes such as 2-chloro-1,3-, 1-chloro-2,4-dinitrobenzene, o-, m-, p-chloronitrobenzene, 1,2-dichloro-4-, 1,4-dichloro-2-, 2,4-dichloro-1- and 1,2-dichloro-3-nitrobenzene, chloronitrotoluenes such as 4-chloro-2-, 4-chloro-3-, 2-chloro-4- and 2-chloro-6-nitrotoluene, nitroanilines such as o-, m-, p-nitroaniline; nitro alcohols such as tris(hydroxymethyl)nitromethane, 2-nitro-2-methyl-, 2-nitro-2-ethyl-1,3-propanediol, 2-nitro-1-butanol and 2-nitro-2-methyl-1-propanol, and any mixtures of two or more of the abovementioned nitro compounds.

The process of the present invention is preferably used to hydrogenate aromatic nitro compounds, preferably mononitrobenzene, methylnitrobenzene or dimethyldinitrobenzene and in particular 2,4-dinitrotoluene or its industrial mixtures with 2,6-dinitrotoluene, which mixtures preferably contain up to 35% by weight, based on the total mixture, of 2,6-dinitrotoluene with proportions of from 1 to 4 percent of vicinal DNT and from 0.5 to 1.5% of 2,5- and 3,5-dinitrotoluene, to form the corresponding amines.

In the process of the present invention, the aromatic and/or aliphatic nitro compound, preferably dinitro and/or polynitro compound, can be used in pure form, as a mixture with the corresponding diamine and/or polyamine, as a mixture with the corresponding diamine and/or polyamine and water, as a mixture with the corresponding diamine and/or polyamine, water and an alcoholic solvent or as a mixture with the corresponding diamine and/or polyamine, water, an alcoholic solvent and a catalyst-reactivating additive, where in each case mixtures of two or more of the abovementioned nitro compounds, the corresponding amine compounds, the alcoholic solvent and the catalyst-reactivating additive can also be used.

If a mixture as described above is used, the ratio of amine compound to water is preferably in the range from 10:1 to 1:10, particularly preferably in the range from 2:1 to 1:2 and the ratio of the amine/water mixture to at least one alcoholic solvent is preferably from 500:1 to 1:1, particularly preferably from 50:1 to 5:1.

As indicated by what has been said above, the hydrogenation in the process of the present invention can be carried out in the absence or in the presence of an alcoholic solvent and a catalyst-reactivating additive.

If an alcoholic solvent and a catalyst-reactivating additive are used, it is of course also possible to add mixtures of two or more thereof.

Alcoholic solvents used are lower aliphatic alcohols having from 1 to 6 carbon atoms, preferably methanol, ethanol or propanol, either individually or as a mixture of two or more thereof.

As catalyst-reactivating additives, preference is given to using aprotic solvents, in particular acetone, DMF, dioxane or THF or a mixture of two or more thereof.

The amount of the alcoholic solvents used and of the catalyst-reactivating additives is not restricted in any particular way in the process of the present invention and can be freely chosen according to requirements.

However, surprisingly, it is also possible to carry out the hydrogenation of aromatic nitro compounds by the process of the present invention without the use of solvents. This method of carrying out the process simplifies the work-up of the reaction mixture after the hydrogenation and, in addition, secondary reactions with the solvent are completely eliminated.

The process of the present invention is, as indicated above, carried out in the presence of a supported catalyst which comprises nickel as active component, either alone or together with at least one metal of transition group I, V, VI and/or VIII.

The catalysts used according to the present invention can be prepared industrially by applying nickel and, if desired, at least one of the abovementioned additional metals to a suitable support.

As metals of transition group I, V, VI and/or VIII of the Periodic Table, preference is given to using palladium, platinum, rhodium, iron, cobalt, chromium, vanadium, copper, silver or a mixture of two or more thereof.

As support materials, preference is given to using silicon dioxide, silicon carbide, kieselguhr, aluminum oxide, magnesium oxide, titanium dioxide, zirconium dioxide and/or hafnium dioxide or a mixture of two or more thereof, particularly preferably zirconium dioxide, $ZrO_2$—$HfO_2$ and/or $SiO_2$—$ZrO_2$ and/or $SiO_2$—$ZrO_2$—$HfO_2$.

The supports used are preferably mesoporous and have a mean pore diameter of 35–50 nm and a specific surface area of 50–250 $m^2$/g. The surface area of the support is determined by $N_2$ adsorption according to the BET method, particularly in accordance with DIN 66131. The mean pore diameter and the pore size distribution are determined by Hg porosimetry, in particular in accordance with DIN 66133.

The application of nickel and, if desired, the further metal or metals can be achieved by the customary, suitable methods. The supports which have been coated or impregnated with the metal or metal salt are subsequently dried and calcined by known methods. The coated supports are subsequently activated by treating them in a gas stream comprising free hydrogen. This activation usually takes place at from 30 to 600° C., preferably from 80 to 150° C. and particularly preferably at 100° C. The gas stream preferably consists of from 50 to 100% by volume of hydrogen and from 0 to 50% by volume of nitrogen. After reduction at 100° C. for one hour, the catalyst prepared for use according to the present invention has a degree of reduction of at least 70%.

The supported catalysts obtained in this way generally have a nickel metal surface area of from about 10 to about 150 m²/g, preferably from about 20 to about 60 m²/g and a nickel content of generally from about 50 to about 80% by weight, preferably from about 60 to about 75% by weight.

Since these activated catalysts are very reactive and often ignite spontaneously on exposure to atmospheric oxygen or moisture, it is customary to passivate them. This can be achieved, for example, by passing oxygen or carbon dioxide over them.

The supported catalyst used according to the present invention comprises, as indicated above, nickel in a bimodal crystallite size distribution in the range from about 1 to about 200 Angström and having maxima at from about 30 to about 80 Angström and at from about 81 to about 150 Angstrom, with the proportion of finely divided nickel (maxima in the nickel crystallite size distribution at from 30 to 80 Angström) being ≧40%.

The process of the present invention has the advantage that the use of the catalysts described enables the hydrogenation to be carried out without problems and with a high space-time yield in a wide temperature range making maximum use of the high catalytic activity of the catalyst used. The process of the present invention makes it possible to carry out the hydrogenation of nitroaromatics at significantly lower catalyst concentrations in the hydrogenation bath than in the known processes. As a result, considerable catalyst savings compared to the known processes can be achieved. In addition, the low catalyst concentration and the low catalyst input in the process of the present invention enable minimal by-product formation, in particular of tar-like products, to be achieved and thus make possible a higher product purity which leads to a simplified work-up of the hydrogenation products. At the same time, the improved selectivity of the catalyst used according to the present invention results in a higher yield in the range of amine. Compared to the yields in the range of 96–98% which are usual in the prior art, yields of from 98.5 to 99.5% could be achieved in the process of the present invention. The low catalyst content of the hydrogenation products and the lower content of by-products enable the work-up of the hydrogenation products to be simplified. Owing to the low catalyst concentration in the reaction mixture, the disruptions occurring in the known processes as a result of catalyst deposits and blockages in the reaction system are avoided.

In the process of the present invention, the formation of finely divided catalyst material as a result of abrasion, mechanical comminution, etc., can surprisingly also be substantially reduced by means of the special support material. This property of the catalyst is particularly advantageous when the process is carried out in loop reactors, since the catalyst is subject to great mechanical stresses in these. In the separation of the catalyst from the hydrogenation product, only catalytically inactive, poisoned catalyst in finely divided form is discharged from the reactor system during the sedimentation, and then only in small amounts. The use of the special support material likewise enables the degradation of the catalyst support which frequently takes place, also known as leaching, to be largely or completely suppressed. The decisive advantage of the process of the present invention is thus that the catalyst consumption can be significantly reduced. The use of a mechanically and chemically stable catalyst allows the mixing in the reactor to be made very intensive. This makes possible uninhibited mass transfer from and to the catalyst particle. The mechanically and chemically stable catalyst is, in the suspension procedure, broken down significantly more slowly than are the catalysts used in known processes. It can therefore be readily sedimented in the decantation vessel and returned to the reactor. The comminution of the catalyst particles and the associated discharge from the reactor system occur only after such a long period of use that the catalytic activity has already been greatly impaired by the unavoidable influences of catalyst poisons and organic deposits. As a result of the mechanical strength and chemical stability of the catalyst particles and the consequently greatly delayed abrasion and also the absence of agglomeration of hydrogenation-active species, the total amount of catalyst discharged is decreased significantly. This largely eliminates the problems in processing the hydrogenation product. The disruptions caused by caking of catalyst particles in the return system, as are known in the customary processes, are also overcome in the process of the present invention.

The invention is illustrated by the following examples.

EXAMPLE 1

(comparative example)

From 2.7 to 4.0 g/min of dinitrotoluene (DNT, isomer mixture with 2,4/2,6=80/20), from 2.0 to 3.0 1/min of hydrogen and a nickel catalyst having a nickel content of 55% on $SiO_2$, a nickel surface area of 45 m²/g and crystallite sizes of 8–10 nm were fed into a mixture of 750 g of toluenediamine (TDA, isomer mixture with 2,4/2,6=80/20) and 750 g of water in a laboratory hydrogenation reactor having a volume of 2.2 l. The catalyst concentration in the system was 4 g/kg of reaction volume. The hydrogenation activity was from about 40 to about 60 g of DNT/g of catalyst * h. Hydrogenation was carried out pseudocontinuously at 120° C. and a hydrogen pressure of 25 bar. After the reaction was complete, the catalyst was separated from the system and examined by X-ray diffraction. A significant increase in the Ni crystallite size to 16 nm was found. In addition, the formation of Ni-containing silicates was observed. The amine/water mixture was subsequently subjected to distillation. The yield of diamine was, based on dinitrotoluene used, about 96%. 1.6% of low-boiling by-products ("low boilers") and 2.4% of tar-like products ("high boilers") were obtained in the distillative work-up. The content of nitro or amino nitro compounds in the discharged product was less than the detection limit of 10 ppm.

EXAMPLE 2

(according to the present invention)

6.0 g/min of dinitrotoluene (DNT, isomer mixture with 2,4/2,6=80/20), from 4.4 to 4.5 1/min of hydrogen and a nickel catalyst having a nickel content of 65% on $ZrO_2$, a nickel surface area of 55 m²/g and crystallite sizes of 8–9 nm were fed into a mixture of 750 g of toluenediamine (TDA, isomer mixture with 2,4/2,6=80/20) and 750 g of water in a laboratory hydrogenation reactor having a volume of 2.2 l. The catalyst concentration in the system was from about 0.5 to about 1 g/Kg of reaction volume. The hydrogenation activity was ≧360 g of DNT/g of catalyst * h. Hydrogenation was carried out pseudocontinuously at 120° C. and a hydrogen pressure of 25 bar. After the reaction was complete, the catalyst was separated from the system and examined by X-ray diffraction. It was found that the Ni crystallite size had increased only to 10 nm. The formation of nickel-containing compounds was not observed. The amine/water mixture was subsequently subjected to distillation. The yield of diamine was, based on dinitrotoluene used, about 99%. 0.15% of low-boiling by-products ("low boilers") and 0.75% of tar-like products ("high boilers") were obtained in the distillative work-up. The content of nitro or amino nitro compounds in the discharged product was below the detection limit of 10 ppm.

EXAMPLE 3
(comparative example)

From 2.7 to 2.81 metric tons/h of DNT, isomer mixture with 2,4/2,6=80/20, 2.1 standard m$^3$/h of hydrogen and from 1.0 to 1.1 kg/h of SiO$_2$-supported nickel catalyst having a nickel content of 55% by weight, a crystallite size of 8–10 nm and a nickel surface area of 45 m$^2$/g were fed into an amine/water mixture of 11.2 metric tons of TDA, isomer mixture with 2,4/2,6=80/20, and 8.7 metric tons of water in a stirred vessel having a volume of 24 m$^3$ and hydrogenation was carried out continuously at 115° C. and a hydrogen pressure of 25 bar. The hydrogen was fed in countercurrent through the hollow shaft of a turbine stirrer. In a downstream settler, the catalyst was separated off and, after settling, recirculated to the reactor. The hydrogenation bath was subsequently worked up by distillation. The catalyst consumption was about 600 g of catalyst/metric ton of TDA. The yield of diamine was, based on dinitrotoluene used, about 98.4%. 0.5% of low-boiling by-products ("low boilers") and 1.1% of tar-like products ("high boilers") were obtained in the distillative work-up. The content of nitro or amino nitro compounds in the discharged product was below the detection limit of 10 ppm.

EXAMPLE 4
(according to the present invention)

From 2.7 to 2.81 metric tons/h of DNT, isomer mixture with 2,4/2,6=80/20, 2.1 standard m$^3$/h of hydrogen and from 0.6 to 0.65 kg/h of ZrO$_2$-supported nickel catalyst having a nickel content of 68% by weight, a crystallite size of 8–10 nm and a nickel surface area of 55 m$^2$/g were fed into an amine/water mixture of 11.2 metric tons of TDA, isomer mixture with 2,4/2,6=80/20, and 8.7 metric tons of water in a stirred vessel having a volume of 24 m$^3$ and hydrogenation was carried out continuously at 115° C. and a hydrogen pressure of 25 bar. The hydrogen was fed in countercurrent through the hollow shaft of a turbine stirrer. In a downstream settler, the catalyst was separated off and, after settling, recirculated to the reactor. The hydrogenation bath was subsequently worked up by distillation. The catalyst consumption was about 350 g of catalyst/metric ton of TDA. The yield of diamine was, based on dinitrotoluene used, about 99.2%. 0.2% of low-boiling by-products ("low boilers") and 0.6% of tar-like products ("high boilers") were obtained in the distillative work-up. The content of nitro or amino nitro compounds in the discharged product was below the detection limit of 10 ppm.

The examples make it clear that the process of the present invention makes possible a considerable saving in catalyst and an improvement in the amine yield compared to the known processes.

We claim:

1. A process for preparing amines, in which at least one compound containing at least one nitro group is reacted with hydrogen in the presence of a supported catalyst comprising, as catalytically active metal, nickel, optionally together with a least one metal of transition group I, V, VI and/or VIII, wherein the reduced and stabilized supported catalyst comprises nickel crystallites having a bimodal nickel crystallite size distribution having maxima at 30–80 Angström and 81–150 Angström on a support comprising ZrO$_2$, ZrO$_2$—HfO$_2$ and/or SiO$_2$—ZrO$_2$ and/or SiO$_2$—ZrO$_2$—HfO$_2$ and in the reduced and passivated state has a nickel content of 60–80 percent by mass, an SiO$_2$ content of 0–20 percent by mass, a ZrO$_2$ content of 0–40 percent by mass, an HfO$_2$ content of 0–4 percent by mass and after fuirther reduction for one hour at 100° has a degree of reduction of at least 70%.

2. A process as claimed in claim 1, wherein the catalyst is used in an amount of from 0.1 to 5 percent by weight, based on the reaction mixture.

3. A process as claimed in claim 1, wherein the catalyst is used in an amount of from 0.2 to 2 percent by weight, based on the reaction mixture.

4. A process as claimed in claim 1, wherein the reaction is carried out at a temperature in the range from 80 to 200° C.

5. A process as claimed in claim 1, wherein the reaction is carried out at a pressure in the range from 10 to 40 bar.

6. A process as claimed in claim 1, wherein the nitro compounds used have one or more nitro groups and from 1 to 18 carbon atoms in the molecule.

7. A process as claimed in claim 1, wherein the nitro compounds are selected from the group consisting of aliphatic nitro compounds, nitrobenzenes, nitrotoluenes, nitroxylenes, nitronaphthalenes, chloronitrobenzenes, chloronitrotoluenes, nitroanilines, nitro alcohols and mixtures thereof.

8. A process as claimed in claim 1, wherein the nitro compounds comprise aromatic compounds containing one or more nitro groups.

9. A process as claimed in claim 1, wherein the nitro compounds comprise nitrobenzene, nitrotoluene and/or dinitrotoluenes.

10. A process as claimed in claim 1, wherein the reaction is carried out in a stirred vessel.

11. A process as claimed in claim 1, wherein the reaction is carried out in a loop reactor.

12. A process as claimed in claim 1, wherein the reaction is carried out in the absence of an alcoholic solvent.

* * * * *